(12) United States Patent
Seo et al.

(10) Patent No.: US 11,263,304 B2
(45) Date of Patent: Mar. 1, 2022

(54) METHOD AND APPARATUS FOR DECIDING DYSCHROMATOPSIA

(71) Applicant: Netmarble Corporation, Seoul (KR)

(72) Inventors: Il Hwan Seo, Seoul (KR); Hye Jeung Jeung, Seoul (KR); Min Jae Jeon, Seoul (KR)

(73) Assignee: NETMARBLE CORPORATION, Seoul (KR)

( * ) Notice: Subject to any disclaimer, the term of this patent is extended or adjusted under 35 U.S.C. 154(b) by 283 days.

(21) Appl. No.: 16/596,191

(22) Filed: Oct. 8, 2019

(65) Prior Publication Data
US 2020/0110867 A1 Apr. 9, 2020

(30) Foreign Application Priority Data
Oct. 8, 2018 (KR) .......................... 10-2018-0119824

(51) Int. Cl.
*G06F 21/36* (2013.01)
*G06T 11/00* (2006.01)
(Continued)

(52) U.S. Cl.
CPC .............. *G06F 21/36* (2013.01); *G06F 21/31* (2013.01); *G06T 11/001* (2013.01); *G09G 3/2003* (2013.01); *H04L 63/083* (2013.01); *A61B 3/066* (2013.01); *G06F 2221/2133* (2013.01); *G09G 2320/0242* (2013.01)

(58) Field of Classification Search
CPC .. G06F 21/36; G06F 21/31; G06F 2221/2133; H04L 63/083; G06T 11/001; G09G 3/2003; G09G 2320/0242; A61B 3/066
See application file for complete search history.

(56) References Cited

U.S. PATENT DOCUMENTS 10,438,225 B1 * 10/2019 Reading ............. G06Q 30/0225
2002/0065658 A1 * 5/2002 Kanevsky ........... G06F 16/9574
704/260

(Continued)

FOREIGN PATENT DOCUMENTS

JP 2002298133 A 10/2002
JP 2011013973 A 1/2011

*Primary Examiner* — Aravind K Moorthy
(74) *Attorney, Agent, or Firm* — Baker & McKenzie LLP (57) ABSTRACT

A dyschromatopsia deciding method and apparatus is provided. The apparatus includes an I/O interface configured to receive an input for a program, a memory configured to store the input for the program and a processing result of the input, and a processor configured to execute the program, wherein the processor is configured to provide first CAPTCHA information for distinguishing between a person and a machine together with second CAPTCHA information for deciding dyschromatopsia, receive first CAPTCHA input information corresponding to the first CAPTCHA information and second CAPTCHA input information corresponding to the second CAPTCHA information together with authentication information, authenticate a user based on the first CAPTCHA input information, decide dyschromatopsia of the user based on the second CAPTCHA input information, and store a decision result of the dyschromatopsia in response to a decision that the user has the dyschromatopsia.

15 Claims, 11 Drawing Sheets

(51) Int. Cl.
*G09G 3/20* (2006.01)
*H04L 29/06* (2006.01)
*G06F 21/31* (2013.01)
*A61B 3/06* (2006.01)

(56) References Cited

U.S. PATENT DOCUMENTS

| | | | | |
|---|---|---|---|---|
| 2005/0134800 A1* | 6/2005 | Kim | ............ | H04N 9/68 351/242 |
| 2007/0182755 A1* | 8/2007 | Jones | ............ | G06T 11/001 345/592 |
| 2008/0084857 A1* | 4/2008 | Gorti | ............ | H04L 67/02 370/342 |
| 2009/0113294 A1* | 4/2009 | Sanghavi | ............ | G06F 40/103 715/269 |
| 2009/0135266 A1* | 5/2009 | Raaymakers | ............ | A61B 3/066 348/222.1 |
| 2009/0235327 A1* | 9/2009 | Jakobsson | ............ | G06F 21/31 726/2 |
| 2011/0029781 A1* | 2/2011 | Clark | ............ | G06F 21/31 713/182 |
| 2011/0113378 A1* | 5/2011 | Boden | ............ | G06F 21/36 715/837 |
| 2011/0225629 A1* | 9/2011 | Pai | ............ | G06F 21/36 726/3 |
| 2011/0229023 A1* | 9/2011 | Jones | ............ | G06T 5/00 382/162 |
| 2012/0246737 A1* | 9/2012 | Paxton | ............ | G06F 16/24578 726/27 |
| 2012/0254940 A1* | 10/2012 | Raper | ............ | G06F 21/31 726/3 |
| 2013/0014214 A1* | 1/2013 | Garside | ............ | G06F 21/36 726/2 |
| 2013/0042311 A1* | 2/2013 | Broder | ............ | H04L 9/3271 726/7 |
| 2013/0104217 A1* | 4/2013 | Kruger | ............ | G06F 21/31 726/7 |
| 2014/0196133 A1* | 7/2014 | Shuster | ............ | H04L 63/126 726/7 |
| 2014/0196143 A1* | 7/2014 | Fliderman | ............ | G06F 21/32 726/19 |
| 2014/0223547 A1* | 8/2014 | Tse | ............ | G06F 21/46 726/19 |
| 2014/0250538 A1* | 9/2014 | Rapaport | ............ | H04L 63/126 726/28 |
| 2015/0193631 A1* | 7/2015 | Adams | ............ | G06F 21/62 726/30 |
| 2015/0319153 A1* | 11/2015 | Tartz | ............ | H04L 63/08 726/4 |
| 2016/0028730 A1* | 1/2016 | Natarajan | ............ | H04L 63/10 726/6 |
| 2016/0180073 A1* | 6/2016 | Zhou | ............ | G06F 3/0488 726/27 |
| 2016/0226853 A1* | 8/2016 | Wall | ............ | H04L 63/1425 |
| 2016/0261586 A1* | 9/2016 | Huang | ............ | G06T 11/60 |
| 2016/0330235 A1* | 11/2016 | Thompson | ............ | H04L 63/10 |
| 2017/0019407 A1* | 1/2017 | Kwon | ............ | H04L 63/10 |
| 2017/0090569 A1* | 3/2017 | Levesque | ............ | G06F 21/36 |
| 2017/0170967 A1* | 6/2017 | Luo | ............ | G09C 5/00 |
| 2017/0180348 A1* | 6/2017 | Piccolotto | ............ | G06K 9/00355 |
| 2017/0193210 A1* | 7/2017 | Liu | ............ | G06F 21/32 |
| 2017/0262623 A1* | 9/2017 | Plenderleith | ............ | G06F 3/04842 |
| 2017/0272429 A1* | 9/2017 | Munasinghe | ............ | A61B 7/04 |
| 2017/0346804 A1* | 11/2017 | Beecham | ............ | H04L 63/083 |
| 2017/0366547 A1* | 12/2017 | Goldfarb | ............ | H04L 63/102 |
| 2017/0366564 A1* | 12/2017 | Ping | ............ | H04L 63/1425 |
| 2018/0114001 A1* | 4/2018 | Jain | ............ | G06F 21/31 |
| 2018/0203708 A1* | 7/2018 | Carey | ............ | G06F 21/31 |
| 2018/0359233 A1* | 12/2018 | Alexander | ............ | H04L 63/083 |
| 2019/0057206 A1* | 2/2019 | Deng | ............ | G06F 21/36 |
| 2019/0138885 A1* | 5/2019 | Rodriguez Bravo | .. | A61B 5/378 |
| 2019/0305968 A1* | 10/2019 | Versteeg | ............ | H04L 9/3239 |
| 2019/0318352 A1* | 10/2019 | Clark | ............ | G06Q 20/40145 |
| 2019/0384905 A1* | 12/2019 | Yeh | ............ | G06F 21/36 |

* cited by examiner

METHOD AND APPARATUS FOR DECIDING DYSCHROMATOPSIA

CROSS-REFERENCE TO RELATED APPLICATION(S)

This application claims the benefit of Korean Patent Application No. 10-2018-0119824, filed on Oct. 8, 2018, in the Korean Intellectual Property Office, the disclosure of which is incorporated herein by reference.

BACKGROUND

1. Field of the Invention

One or more example embodiments relate to a technology for deciding dyschromatopsia

2. Description of the Related Art

A content providing program may decide dyschromatopsia of a user and complement contents. As an example, the program may specify colors for one or more game objects in response to a user's color setting request. In this example, the program may set a color for at least one game object according to the user's color setting request. The program may display a game object of which a color is designated by a user with the color designated by the user among game objects displayed on a game screen. As another example, one or more content display methods may be prepared in correspondence with a preset color vision characteristic, so that a user selects a degree and one of color vision characteristics set based on color vision characteristics of the user. However, these methods explicitly require an additional process of specifying color vision characteristics, which may increase a barrier to entry of the user for the program.

SUMMARY

According to an aspect, there is provided a dyschromatopsia deciding apparatus including an input and output (I/O) interface configured to receive an input for a program, a memory configured to store the input for the program and a processing result of the input, and a processor configured to execute the program, wherein the processor is configured to provide first completely automated public turing test to tell computers and humans apart (CAPTCHA) information for distinguishing between a person and a machine together with second CAPTCHA information for deciding dyschromatopsia, receive first CAPTCHA input information corresponding to the first CAPTCHA information and second CAPTCHA input information corresponding to the second CAPTCHA information together with authentication information, authenticate a user based on the first CAPTCHA input information, decide dyschromatopsia of the user based on the second CAPTCHA input information, and store a decision result of the dyschromatopsia in response to a decision that the user has the dyschromatopsia.

The first CAPTCHA information and the second CAPTCHA information may be displayed on a same screen or consecutive screens. The processor may be configured to provide again first CAPTCHA information for distinguishing between a person and a machine together with second CAPTCHA information for deciding dyschromatopsia when an authentication of the user fails.

The first CAPTCHA information and the second CAPTCHA information may include at least one of a text CAPTCHA, an image CAPTCHA, and a slide CAPTCHA.

When an authentication of the user fails, the processor may be configured to provide again first CAPTCHA information for distinguishing between a person and a machine together with second CAPTCHA information for deciding dyschromatopsia.

When an authentication of the user is successful, the processor may be configured to decide dyschromatopsia of the user based on the second CAPTCHA input information.

According to another aspect, there is provided a dyschromatopsia compensation apparatus including an I/O interface configured to receive an input for a program, a memory configured to store the input for the program and a processing result of the input, and a processor configured to execute the program, wherein the processor is configured to provide a screen for requesting authentication information of a user, authenticate a user based on the authentication information, load prestored dyschromatopsia information of the user when an authentication of the user is successful, and change a content display scheme of a program based on the dyschromatopsia information, the dyschromatopsia information of the user is acquired based on second CAPTCHA input information received in correspondence to second CAPTCHA information for deciding dyschromatopsia, and first CAPTCHA information for distinguishing between a person and a machine and the second CAPTCHA information are provided together on the screen.

The processor may be configured to change color information of contents based on the dyschromatopsia information when the user has the dyschromatopsia.

The processor may be configured to change texture information of contents based on the dyschromatopsia information when the user has the dyschromatopsia.

According to another aspect, there is provided a dyschromatopsia deciding method of a program for displaying contents, the method including providing first CAPTCHA information for distinguishing between a person and a machine together with second CAPTCHA information for deciding dyschromatopsia, receiving first CAPTCHA input information corresponding to the first CAPTCHA information and second CAPTCHA input information corresponding to the second CAPTCHA information together with authentication information, authenticating a user based on the first CAPTCHA input information and deciding dyschromatopsia of the user based on the second CAPTCHA input information, and storing a decision result of the dyschromatopsia in response to a decision that the user has the dyschromatopsia.

The first CAPTCHA information and the second CAPTCHA information may include at least one of a text CAPTCHA, an image CAPTCHA, and a slide CAPTCHA.

The deciding may include authenticating the user based on the first CAPTCHA input information and providing again first CAPTCHA information for distinguishing between a person and a machine and second CAPTCHA information for deciding dyschromatopsia when an authentication of the user fails.

The deciding may include authenticating the user based on the first CAPTCHA input information and deciding dyschromatopsia of the user based on the second CAPTCHA input information when an authentication of the user is successful.

According to another aspect, there is provided a dyschromatopsia compensation method of a program for displaying contents, the method including providing a screen for requesting authentication information of a user, authenticating a user based on the authentication information, loading prestored dyschromatopsia information of the user when an authentication of the user is successful, and changing a content display scheme of a program based on the dyschromatopsia information, wherein the dyschromatopsia information of the user is acquired based on second CAPTCHA input information received in correspondence to second CAPTCHA information for deciding dyschromatopsia provided together with first CAPTCHA information for distinguishing between a person and a machine.

The first CAPTCHA information and the second CAPTCHA information may be provided together on the screen.

When the user has the dyschromatopsia, the changing of the content display scheme may change color information of contents based on the dyschromatopsia information.

When the user has the dyschromatopsia, the changing of the content display scheme may change texture information of contents based on the dyschromatopsia information.

According to another aspect, there is provided a method of providing a user interface, the method including defining a first user interface area in which first CAPTCHA information for distinguishing between a person and a machine is displayed, on one side of a display, defining a second user interface area in which second CAPTCHA information for deciding dyschromatopsia of a user is displayed, on another side of the display, visually displaying the first user interface area and the second user interface area on a same screen or consecutive screens, visually displaying the first user interface area and the second user interface area on the same screen or consecutive screens when the user is not authenticated as a person based on first CAPTCHA input information corresponding to first CAPTCHA information, and visually displaying whether the user has dyschromatopsia by analyzing second CAPTCHA input information corresponding to the second CAPTCHA information when the user is authenticated as a person based on the first CAPTCHA input information corresponding to the first CAPTCHA information.

The first user interface area and the second user interface area may be adjacent to each other.

A non-transitory computer-readable storage medium may store instructions that, when executed by a processor, cause the processor to perform the dyschromatopsia deciding method of claim 10.

A computer program may be stored in a storage medium for executing the method in combination with a computer.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

The following structural or functional descriptions of example embodiments described herein are merely intended for the purpose of describing the example embodiments described herein and may be implemented in various forms. However, it should be understood that these example embodiments are not construed as limited to the illustrated forms.

Various modifications may be made to the example embodiments. Here, the examples are not construed as limited to the disclosure and should be understood to include all changes, equivalents, and replacements within the idea and the technical scope of the disclosure.

Although terms of "first," "second," and the like are used to explain various components, the components are not limited to such terms. These terms are used only to distinguish one component from another component. When it is mentioned that one component is "connected" or "accessed" to another component, it may be understood that the one component is directly connected or accessed to another component or that still other component is interposed between the two components.

The terminology used herein is for the purpose of describing particular embodiments only and is not intended to be limiting. As used herein, the singular forms are intended to include the plural forms as well, unless the context clearly indicates otherwise. It will be further understood that the terms "comprises" and/or "comprising," when used in this specification, specify the presence of stated features, integers, steps, operations, elements, components or a combination thereof, but do not preclude the presence or addition of one or more other features, integers, steps, operations, elements, components, and/or groups thereof.

Unless otherwise defined herein, all terms used herein including technical or scientific terms have the same meanings as those generally understood by one of ordinary skill in the art. Terms defined in dictionaries generally used should be construed to have meanings matching contextual meanings in the related art and are not to be construed as an ideal or excessively formal meaning unless otherwise defined herein.

Hereinafter, example embodiments will be described in detail with reference to the accompanying drawings. The scope of the right, however, should not be construed as limited to the example embodiments set forth herein. Like reference numerals in the drawings refer to like elements throughout the present disclosure.

Figure 1:
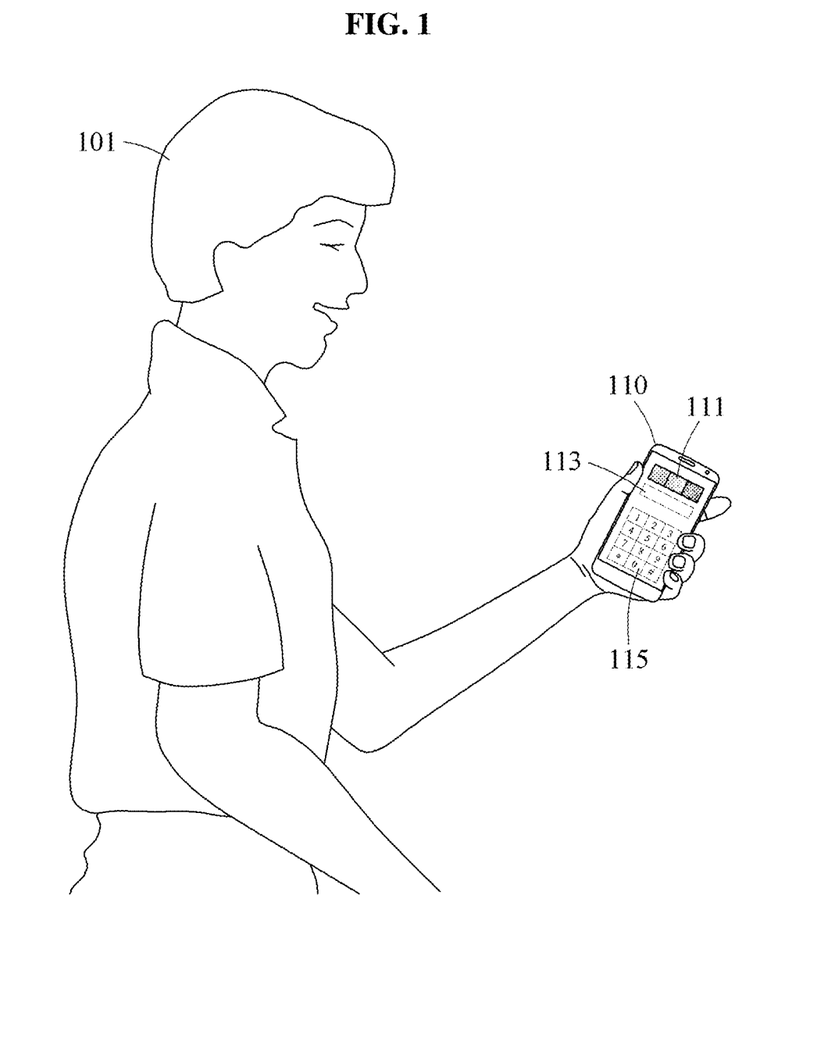
FIG. 1 is a diagram illustrating an example of a situation in which dyschromatopsia of a user is decided by a dyschromatopsia deciding apparatus according to an example embodiment.

FIG. 1 is a diagram illustrating an example of a situation in which dyschromatopsia of a user is decided by a dyschromatopsia deciding apparatus according to an example embodiment.

A quality of a display and graphics of a terminal has been steadily developing and, accordingly, a desire for visual quality of a user is also increasing. Expressing a variety of colors is one of important factors required in various programs including a game program.

Meanwhile, some users have dyschromatopsia. According to a statistics, it is known that 5.9% of males and 0.44% of females have the dyschromatopsia in Korea. A user with the dyschromatopsia may not distinguish a particular color.

To solve this, in a general program, when a user has the dyschromatopsia, the user may inform that the user has the dyschromatopsia or whether the user has the dyschromatopsia may be determined through a separate simple test.

However, when a separate procedure is required for execution of the game program, a satisfaction of the user may decrease. For example, there is a statistics indicating that in a case in which a procedure such as a tutorial is mandatorily executed, a dissatisfaction of the user increases, which may increase a probability of the user leaving the game. As such, when a separate procedure is required to decide whether the user has the dyschromatopsia, a probability of the user leaving the game may increase.

A dyschromatopsia deciding apparatus 110 may decide dyschromatopsia of a user 101. The dyschromatopsia deciding apparatus 110 may naturally decide the dyschromatopsia of the user 101 based on completely automated public turing test to tell computers and humans apart (CAPTCHA) information 111 used in a login process and the like. Through this, the dyschromatopsia deciding apparatus 110 may decide the dyschromatopsia of the user 101 without need to perform a separate process for deciding the dyschromatopsia.

For this, the dyschromatopsia deciding apparatus 110 may include a user interface 113 to input the CAPTCHA information 111 and input information corresponding to the CAPTCHA information 111 through a display, and an input device 115 to input information. Here, the input device 115 may be, for example, a touch pad but not be limited thereto. Instead, a microphone included in the dyschromatopsia deciding apparatus 110 may also be used.

For example, among various types of color vision tests, a pseudoisochromatic plate test may be used in display information for deciding the dyschromatopsia used in the CAPTCHA information 111. A pseudoisochromatic plate may be a table in which a number or figure composed of the same color points are arranged with color points in similar colors so as to confuse a viewer. A person with a normal color vision may easily recognize the number or figure while a person with the dyschromatopsia may not distinguish the color representing the number or figure from the colors therearound. The pseudoisochromatic plate test is merely an example and thus, arrangement tests, anomaloscopes, or lantern tests may also be used.

The dyschromatopsia deciding apparatus 110 may replace an image of CAPTCHA information used for macro detection in a member registration or login process with an image of the pseudoisochromatic plate test, thereby naturally combining an original goal and a decision of the dyschromatopsia.

Figure 2:
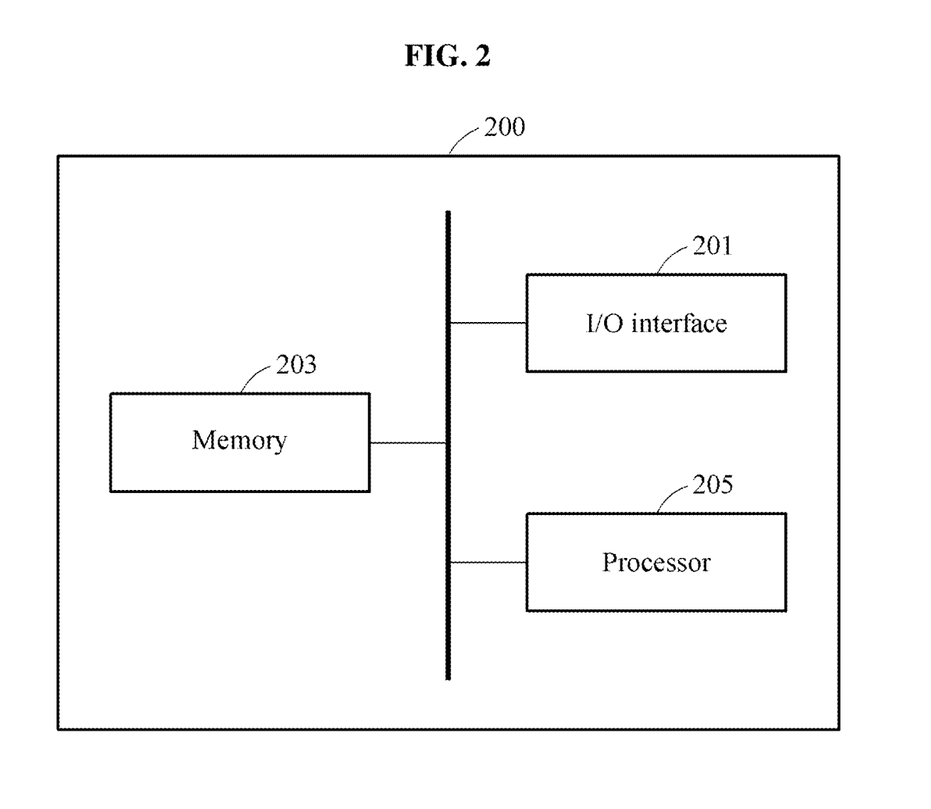
FIG. 2 is a block diagram illustrating a dyschromatopsia deciding apparatus according to an example embodiment.

FIG. 2 is a block diagram illustrating a dyschromatopsia deciding apparatus according to an example embodiment.

A dyschromatopsia deciding apparatus 200 may include an input and output (I/O) interface 201 that receives an input for a program, a memory 203 that stores the input for the program and a processing result of the input, and a processor 205 that executes the program.

The processor 205 may provide first CAPTCHA information for distinguishing between a person and a machine together with second CAPTCHA information for deciding dyschromatopsia. The first CAPTCHA information may be information for determining whether a macro is used in a member registration or login process. However, this is merely an example, and information used for purposes other than the member registration or login process may also be included therein. The first CAPTCHA information and the second CAPTCHA information may include at least one of a text CAPTCHA, an image CAPTCHA, and a slide CAPTCHA.

The processor 205 may receive first CAPTCHA input information corresponding to the first CAPTCHA information and second CAPTCHA input information corresponding to the second CAPTCHA information together with authentication information. The first CAPTCHA input information and the second CAPTCHA input information may each be an input corresponding to a text, an audio, an image, or a slide.

For example, when CAPTCHA information using a pseudoisochromatic plate is provided among dyschromatopsia deciding methods, the second CAPTCHA information may be provided as a combination from which a normal person and a person with dyschromatopsia see different numbers, a combination which is visible only to a normal person, a combination which may be blurry to a person with a color vision deficiency and is invisible to a color blind person, a combination from which a normal person sees two digits and a person with dyschromatopsia see one digit, and the like.

The processor 205 may decide dyschromatopsia of the user based on the second CAPTCHA input information. A reference for deciding dyschromatopsia may be determined based on the dyschromatopsia deciding method. The processor 205 may decide whether the user has the dyschromatopsia based on the reference determined based on the dyschromatopsia deciding method. The processor 205 may store a decision result of the dyschromatopsia.

The processor 205 may authenticate a user based on the first CAPTCHA input information. When an authentication of the user fails, the processor 205 may provide again first CAPTCHA information for distinguishing between a person and a machine together with second CAPTCHA information for deciding dyschromatopsia.

The processor 205 may authenticate a user based on the first CAPTCHA input information. When an authentication of the user is successful, the processor 205 may decide dyschromatopsia of the user based on the second CAPTCHA input information.

Figure 3:
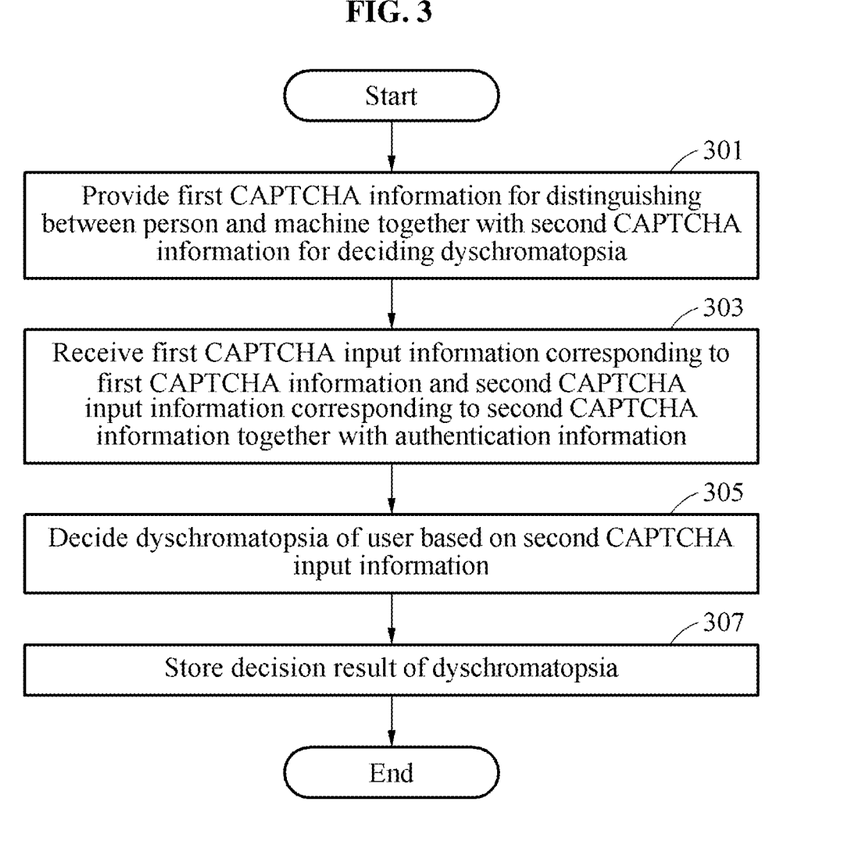
FIG. 3 is a flowchart illustrating operations of a dyschromatopsia deciding method according to an example embodiment.

FIG. 3 is a flowchart illustrating operations of a dyschromatopsia deciding method according to an example embodiment.

In operation 301, the dyschromatopsia deciding apparatus 200 may provide first CAPTCHA information for distinguishing between a person and a machine together with second CAPTCHA information for deciding dyschromatopsia.

In operation 303, the dyschromatopsia deciding apparatus 200 may receive first CAPTCHA input information corresponding to the first CAPTCHA information and second CAPTCHA input information corresponding to the second CAPTCHA information together with authentication information.

In operation 305, the dyschromatopsia deciding apparatus 200 may decide dyschromatopsia of the user based on the second CAPTCHA input information.

In operation 307, the dyschromatopsia deciding apparatus 200 may store a decision result of the dyschromatopsia.

The first CAPTCHA information and the second CAPTCHA information may include at least one of a text CAPTCHA, an image CAPTCHA, and a slide CAPTCHA.

In order to decide the dyschromatopsia, the dyschromatopsia deciding apparatus 200 may authenticate a user based on the first CAPTCHA input information. When an authentication of the user fails, the dyschromatopsia deciding apparatus 200 may provide again first CAPTCHA information for distinguishing between a person and a machine together with second CAPTCHA information for deciding dyschromatopsia.

In order to decide the dyschromatopsia, the dyschromatopsia deciding apparatus 200 may authenticate a user based on the first CAPTCHA input information. When an authentication of the user is successful, the dyschromatopsia deciding apparatus 200 may decide dyschromatopsia of the user based on the second CAPTCHA input information.

Figure 4:
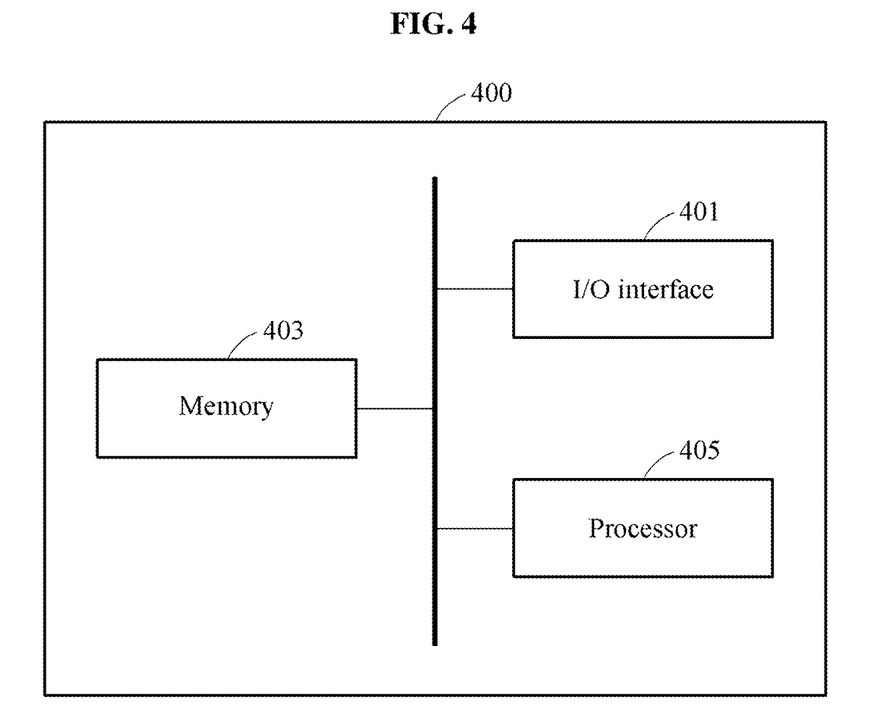
FIG. 4 is a block diagram illustrating a dyschromatopsia compensation apparatus according to an example embodiment.

FIG. 4 is a block diagram illustrating a dyschromatopsia compensation apparatus according to an example embodiment.

A dyschromatopsia compensation apparatus 400 may include an I/O interface 401 that receives an input for a program, a memory 403 that stores the input for the program and a processing result of the input, and a processor 405 that executes the program.

The dyschromatopsia compensation apparatus 400 may provide a screen for requesting authentication information of a user and authenticate a user based on the authentication information.

When an authentication of the user is successful, the dyschromatopsia compensation apparatus 400 may load prestored dyschromatopsia information of the user.

The dyschromatopsia compensation apparatus 400 may change a content display scheme of a program based on the dyschromatopsia information.

Here, the dyschromatopsia information of the user may be acquired based on second CAPTCHA input information received in correspondence to second CAPTCHA information for deciding dyschromatopsia provided together with first CAPTCHA information for distinguishing between a person and a machine.

When the user has the dyschromatopsia, the dyschromatopsia compensation apparatus 400 may change color information of contents based on the dyschromatopsia information.

When the user has the dyschromatopsia, the dyschromatopsia compensation apparatus 400 may change texture information of contents based on the dyschromatopsia information.

Figure 5:
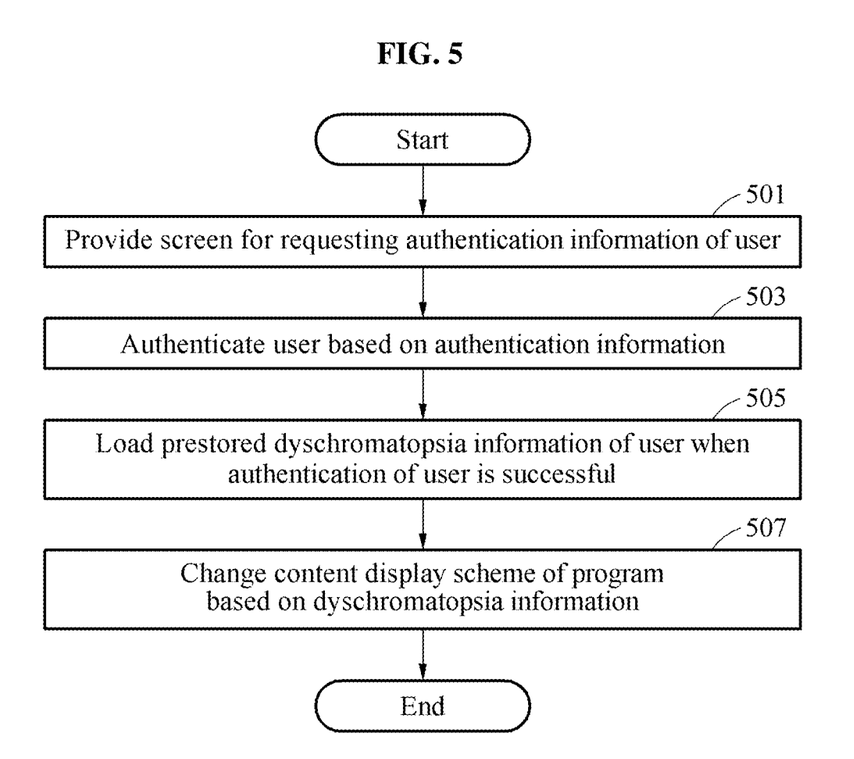
FIG. 5 is a flowchart illustrating operations of a dyschromatopsia compensation method according to an example embodiment.

FIG. 5 is a flowchart illustrating operations of a dyschromatopsia compensation method according to an example embodiment.

In operation 501, the dyschromatopsia compensation apparatus 400 may provide a screen for requesting authentication information of a user.

In operation 503, the dyschromatopsia compensation apparatus 400 may authenticate a user based on the authentication information.

In operation 505, the dyschromatopsia compensation apparatus 400 may load prestored dyschromatopsia information of the user when an authentication of the user is successful.

In operation 507, the dyschromatopsia compensation apparatus 400 may change a content display scheme of a program based on the dyschromatopsia information.

The dyschromatopsia information of the user may be acquired based on second CAPTCHA input information received in correspondence to second CAPTCHA information for deciding dyschromatopsia provided together with first CAPTCHA information for distinguishing between a person and a machine.

In order to change the content display scheme, when the user has the dyschromatopsia, the dyschromatopsia compensation apparatus 400 may change color information of contents based on the dyschromatopsia information.

In order to change the content display scheme, when the user has the dyschromatopsia, the dyschromatopsia compensation apparatus 400 may change texture information of contents based on the dyschromatopsia information.

Figure 6:
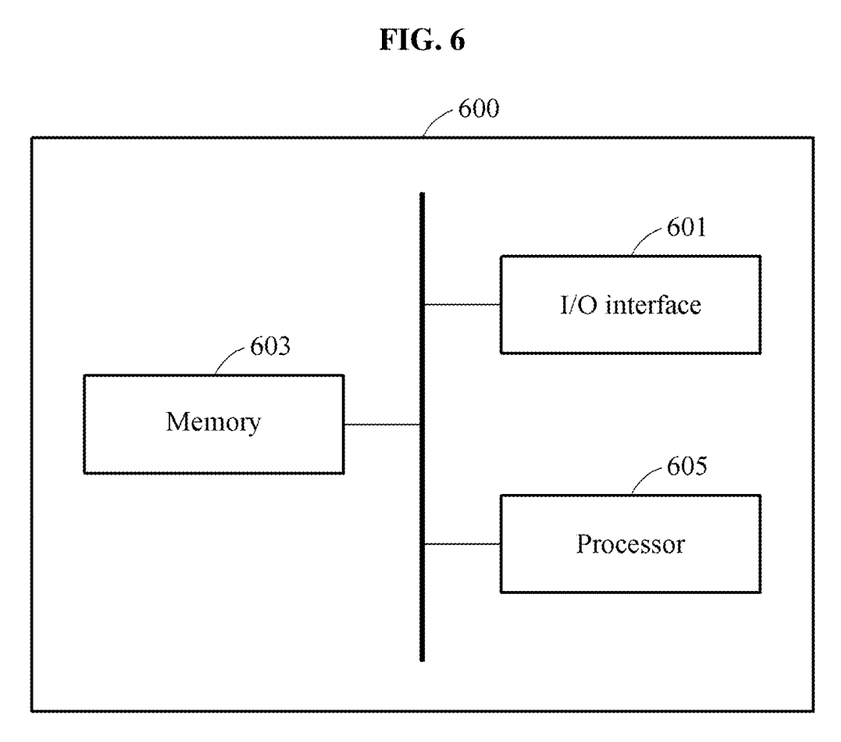
FIG. 6 is a block diagram illustrating a user interface providing apparatus according to an example embodiment.

FIG. 6 is a block diagram illustrating a user interface providing apparatus according to an example embodiment.

A user interface providing apparatus 600 may include an I/O interface 601, a memory 603, and a processor 605.

The processor 605 may define a first user interface area in which first CAPTCHA information for distinguishing between a person and a machine is displayed, on one side of a display.

The processor 605 may define a second user interface area in which second CAPTCHA information for deciding dyschromatopsia of a user is displayed, on another side of the display.

The processor 605 may visually display the first user interface area and the second user interface area on a same screen or consecutive screens.

When the user is not authenticated as a person based on first CAPTCHA input information corresponding to first CAPTCHA information, the processor 605 may visually display the first user interface area and the second user interface area on the same screen or consecutive screens.

When the user is authenticated as a person based on the first CAPTCHA input information corresponding to the first CAPTCHA information, the processor 605 may visually display whether the user has dyschromatopsia by analyzing second CAPTCHA input information corresponding to the second CAPTCHA information.

Figure 7:
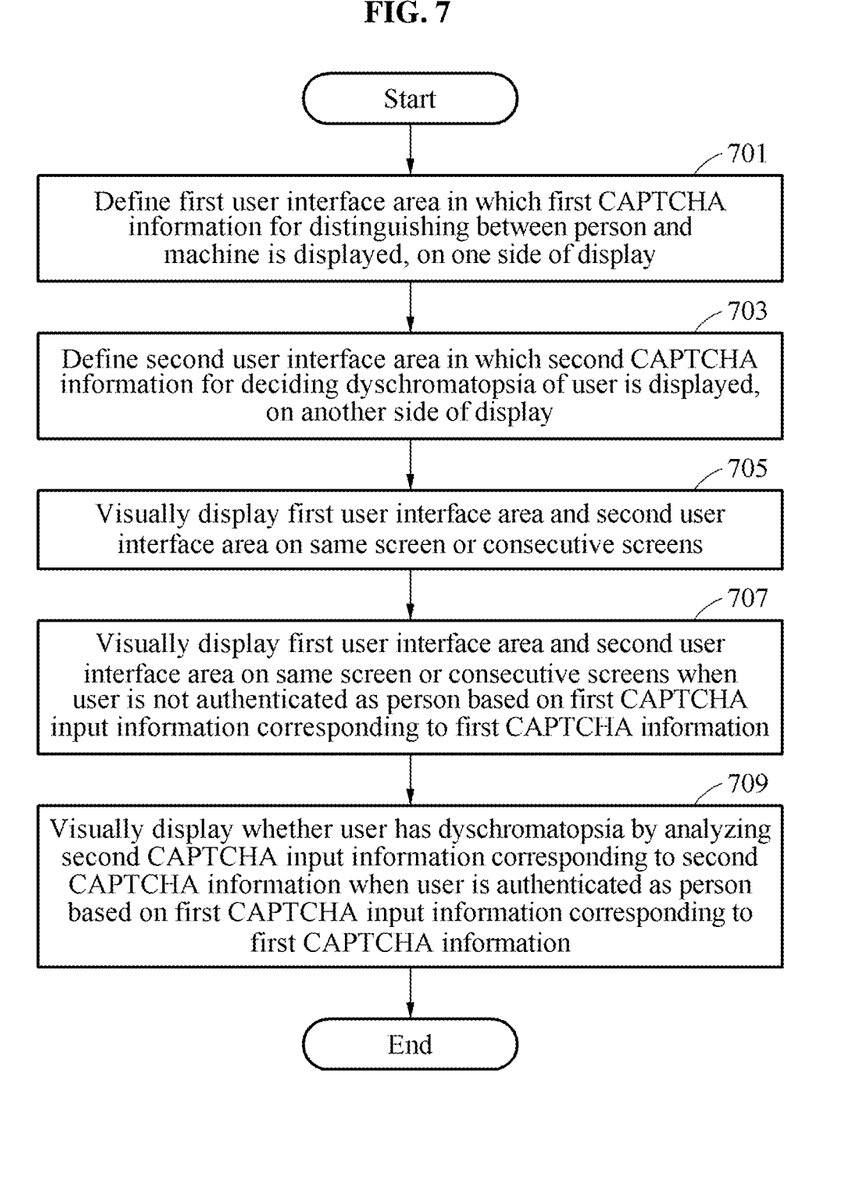
FIG. 7 is a flowchart illustrating operations of a method of providing a user interface according to an example embodiment.

FIG. 7 is a flowchart illustrating operations of a method of providing a user interface according to an example embodiment.

In operation 701, the user interface providing apparatus 600 may define a first user interface area in which first CAPTCHA information for distinguishing between a person and a machine is displayed, on one side of a display.

In operation 703, the user interface providing apparatus 600 may define a second user interface area in which second CAPTCHA information for deciding dyschromatopsia of a user is displayed, on another side of the display.

In operation 705, the user interface providing apparatus 600 may visually display the first user interface area and the second user interface area on a same screen or consecutive screens.

In operation 707, when the user is not authenticated as a person based on first CAPTCHA input information corresponding to first CAPTCHA information, the user interface providing apparatus 600 may visually display the first user interface area and the second user interface area on the same screen or consecutive screens.

In operation 709, when the user is authenticated as a person based on the first CAPTCHA input information corresponding to the first CAPTCHA information, the user interface providing apparatus 600 may visually display whether the user has dyschromatopsia by analyzing second CAPTCHA input information corresponding to the second CAPTCHA information.

Figure 8:
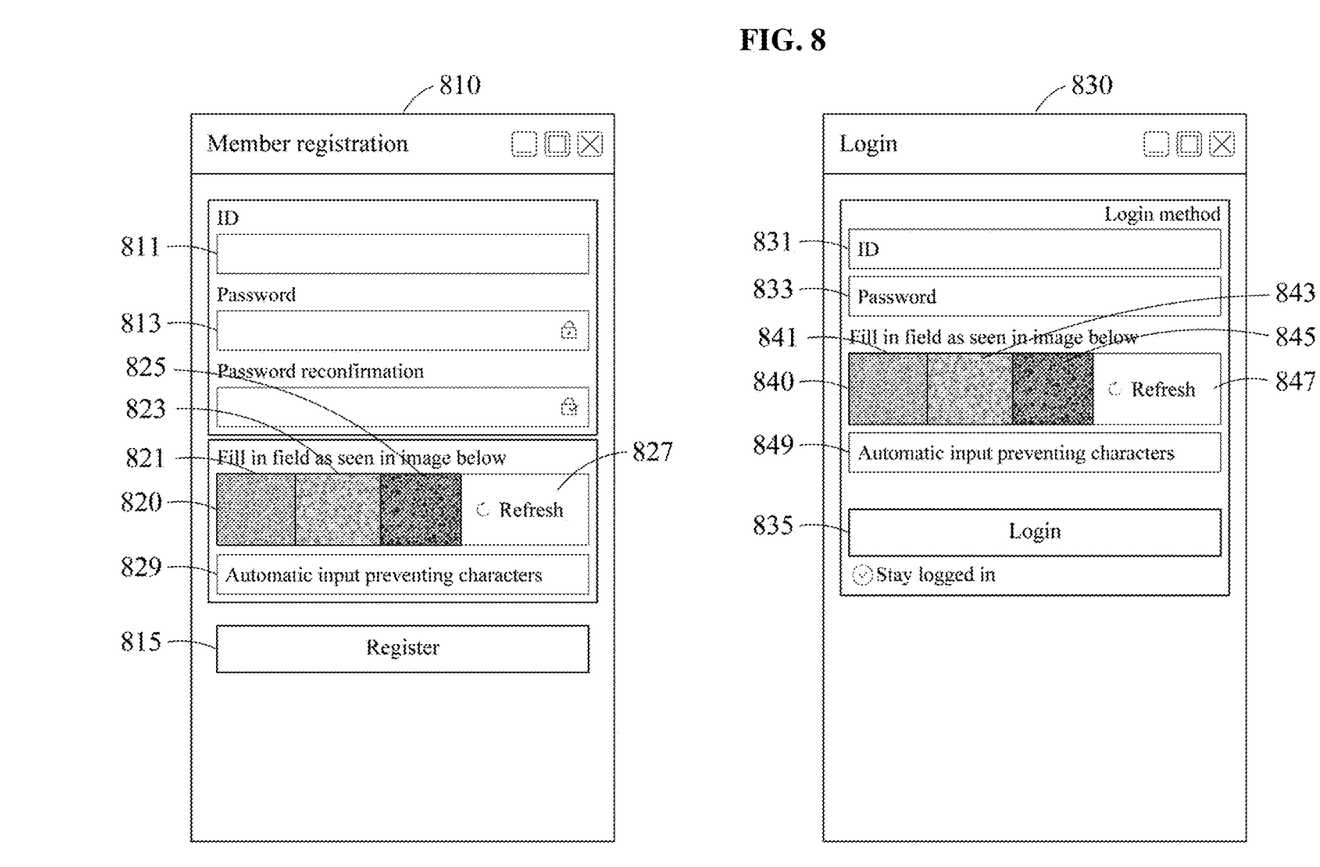
FIG. 8 is a diagram illustrating an example of a user interface of a dyschromatopsia deciding apparatus according to an example embodiment.

FIG. 8 is a diagram illustrating an example of a user interface of a dyschromatopsia deciding apparatus according to an example embodiment.

Referring to FIG. 8, a user interface 810 may provide a screen for member registration. The user interface 810 may include an identification (ID) field 811, a password field 813, a password reconfirmation field, a CAPTCHA information display field 820, a CAPTCHA information field 829, and a "sign-up" button 815.

Here, the CAPTCHA information display field 820 may include CAPTCHA information 821 for automatic input prevention and CAPTCHA information 823 and 825 for deciding dyschromatopsia. The CAPTCHA information display field 820 may further include a refresh button 827.

A user interface 830 may provide a screen for login. The user interface 830 may include an ID field 831, a password field 833, a CAPTCHA information display field 840, a CAPTCHA information field 849, and a login button 835.

Here, the CAPTCHA information display field 840 may include CAPTCHA information 841 for automatic input prevention and CAPTCHA information 843 and 845 for deciding dyschromatopsia. The CAPTCHA information display field 840 may further include a refresh button 847.

Figure 9:
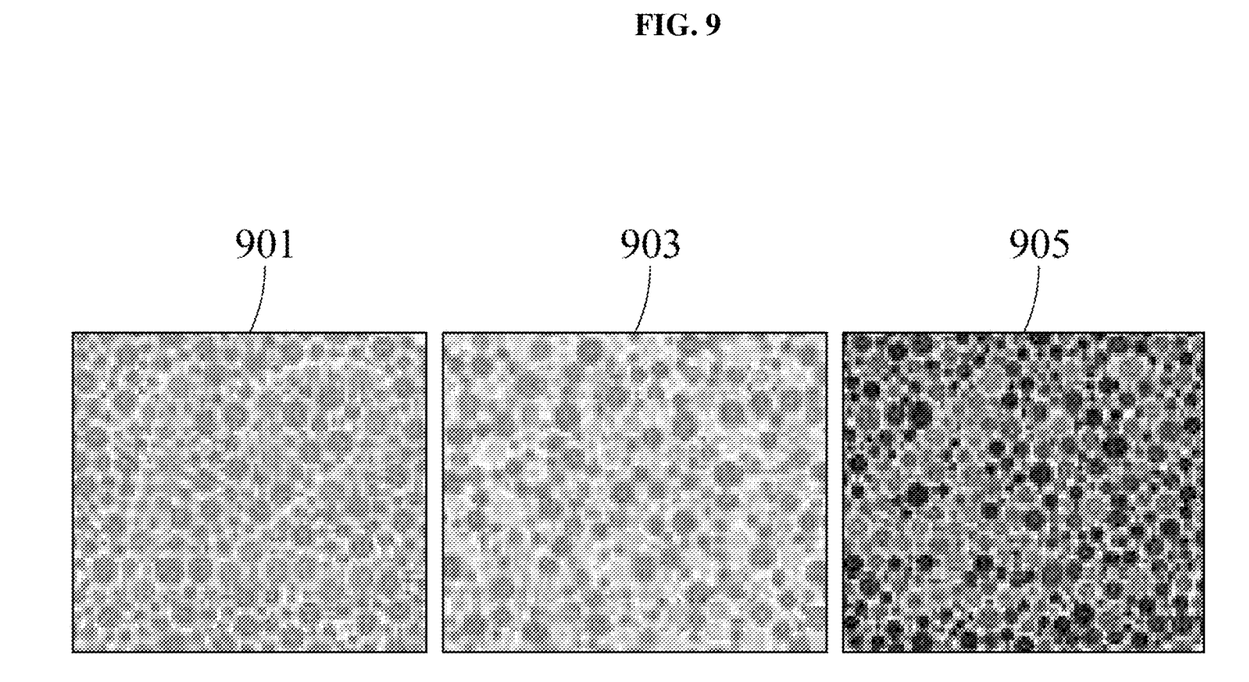
FIG. 9 is a diagram illustrating an example of a CAPTCHA of a user interface of a dyschromatopsia deciding apparatus according to an example embodiment.

FIG. 9 is a diagram illustrating an example of a CAPTCHA of a user interface of a dyschromatopsia deciding apparatus according to an example embodiment.

A user interface provided by a dyschromatopsia deciding apparatus may include CAPTCHA information. The CAPTCHA information may include CAPTCHA information for deciding dyschromatopsia in addition to macro-protecting CAPTCHA information for member registration or login.

FIG. 9 illustrates CAPTCHA information using a pseudoisochromatic plate among dyschromatopsia deciding methods. Captcha information 901 may indicate a color table (first type) that can be read by everyone irrespective of dyschromatopsia. Captcha information 903 and CAPTCHA information 905 may include, for example, a combination from which a normal person and a person with dyschromatopsia see different numbers, a combination which is visible only to a normal person, a combination which may be blurry to a person with a color vision deficiency and is invisible to a color blind person, and a combination from which a normal person sees two digits and a person with dyschromatopsia see one digit.

For example, when an input of a user is "122942", the user may be determined to be a person with a normal color vision. When an input of a user is "110040", the input may be determined to be an input by macro. In this case, the CAPTCHA information may be provided through a replacement. When an input of a user is "12704", the user may be determined to be a user with a red-green color blindness. When an input of a user is "12", the user may be determined to be a color blind person.

Figure 10:
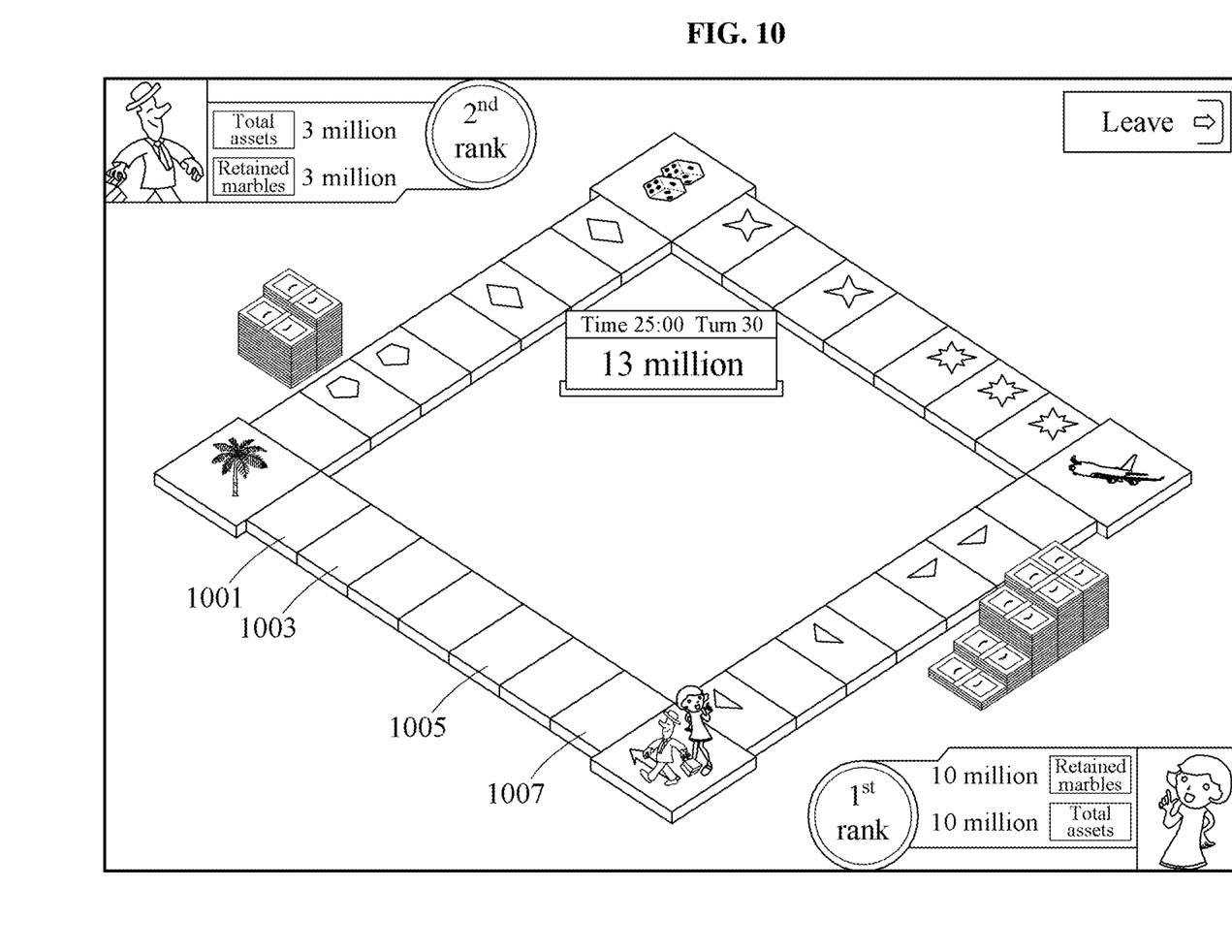
FIG. 10 is a diagram illustrating an example of contents complemented by a dyschromatopsia compensation apparatus according to an example embodiment.
Figure 11:
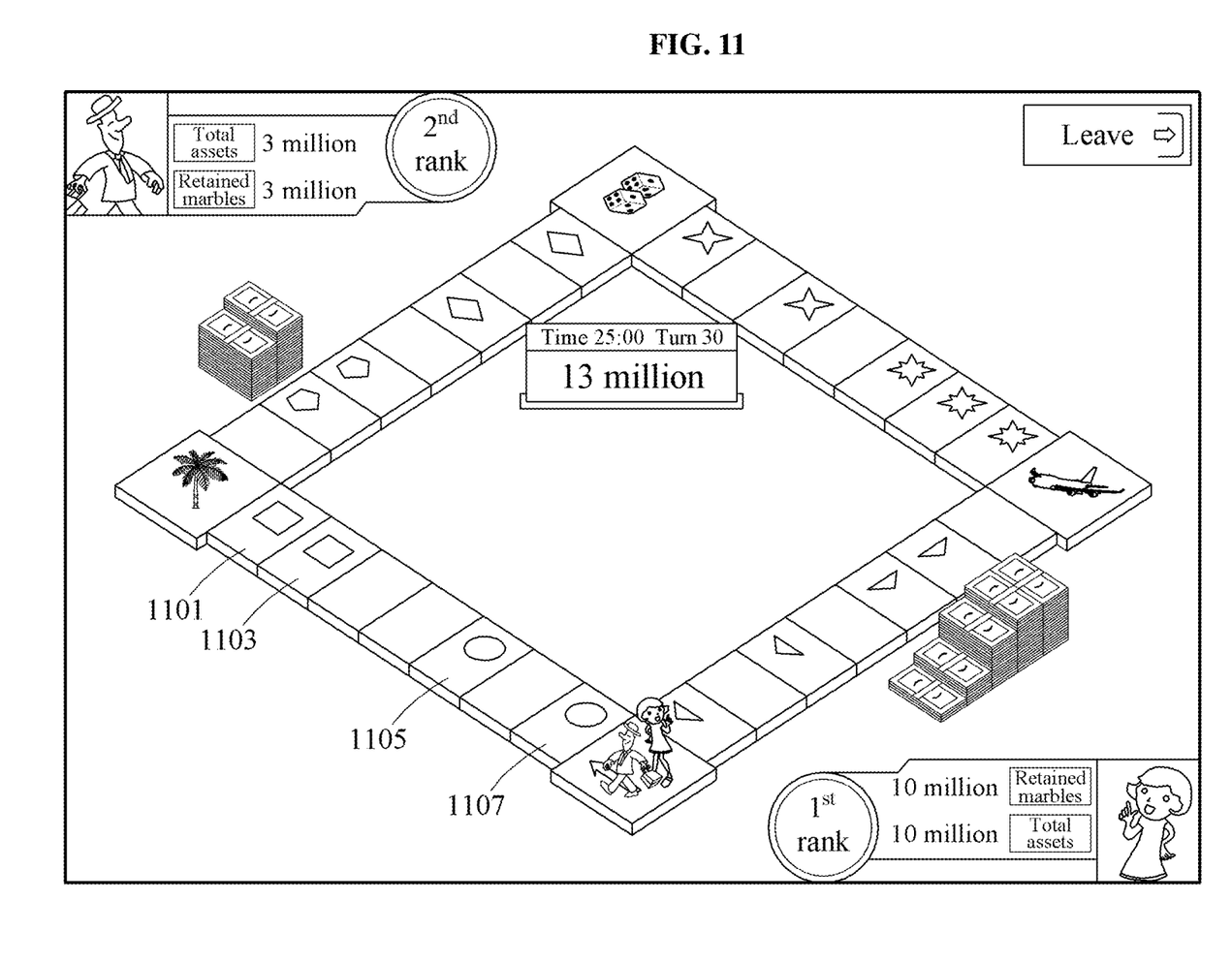
FIG. 11 is a diagram illustrating another example of contents complemented by a dyschromatopsia compensation apparatus according to an example embodiment.

FIG. 10 is a diagram illustrating an example of contents complemented by a dyschromatopsia compensation apparatus according to an example embodiment. FIG. 11 is a diagram illustrating another example of contents complemented by a dyschromatopsia compensation apparatus according to an example embodiment.

Referring to FIG. 10, when it is decided that a user has dyschromatopsia, a dyschromatopsia compensation apparatus may change a color of content. For example, the dyschromatopsia compensation apparatus may change contents 1001, 1003, 1005, and 1007 represented by a combination of colors that are not to be distinguished by a person having the dyschromatopsia, to the contents 1001, 1003, 1005, and 1007 represented by a combination of colors to be distinguished by the person having the dyschromatopsia.

Referring to FIG. 11, when it is determined that a user has dyschromatopsia, a dyschromatopsia compensation apparatus may change a color of content. For example, the dyschromatopsia compensation apparatus may change contents 1101, 1103, 1105, and 1107 represented by a combination of colors that are not to be distinguished by a person having the dyschromatopsia, to the contents 1101, 1103, 1105, and 1107 represented by a combination of patterns to be distinguished by the person having the dyschromatopsia.

The units described herein may be implemented using a hardware component, a software component and/or a combination thereof. A processing device may be implemented using one or more general-purpose or special purpose computers, such as, for example, a processor, a controller and an arithmetic logic unit (ALU), a DSP, a microcomputer, an FPGA, a programmable logic unit (PLU), a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A dyschromatopsia deciding apparatus comprising:
    an input and output (I/O) interface configured to receive an input for a program;
    a non-transitory memory configured to store the input for the program and a processing result of the input; and
    a processor configured to execute the program,
    wherein the processor is configured to:
    provide first completely automated public turing test to tell computers and humans apart (CAPTCHA) information for distinguishing between a person and a machine together with second CAPTCHA information for deciding dyschromatopsia;
    receive first CAPTCHA input information corresponding to the first CAPTCHA information and second CAPTCHA input information corresponding to the second CAPTCHA information together with authentication information;
    authenticate a user based on the first CAPTCHA input information;
    decide dyschromatopsia of the user based on the second CAPTCHA input information; and
    store a decision result of the dyschromatopsia in response to a decision that the user has the dyschromatopsia;
    wherein the first CAPTCHA information and the second CAPTCHA information are displayed on a same screen or consecutive screens, and
    wherein first CAPTCHA information for distinguishing between a person and a machine is provided again together with second CAPTCHA information for deciding dyschromatopsia when an authentication of the user fails.

2. The dyschromatopsia deciding apparatus of claim 1, wherein the first CAPTCHA information and the second CAPTCHA information include at least one of a text CAPTCHA, an image CAPTCHA, and a slide CAPTCHA.

3. The dyschromatopsia deciding apparatus of claim 1, wherein when an authentication of the user is successful, the processor is configured to decide dyschromatopsia of the user based on the second CAPTCHA input information.

4. A dyschromatopsia compensation apparatus comprising:
    an input and output (I/O) interface configured to receive an input for a program;
    a non-transitory memory configured to store the input for the program and a processing result of the input; and
    a processor configured to execute the program,
    wherein the processor is configured to:
    provide a screen for requesting authentication information of a user;
    authenticate a user based on the authentication information;
    load prestored dyschromatopsia information of the user when an authentication of the user is successful; and
    change a content display scheme of a program based on the dyschromatopsia information,
    wherein the dyschromatopsia information of the user is acquired based on second completely automated public turing test to tell computers and humans apart (CAPTCHA) input information received in correspondence to second CAPTCHA information for deciding dyschromatopsia, and
    wherein first CAPTCHA information for distinguishing between a person and a machine and the second CAPTCHA information are provided together on the screen,
    wherein the first CAPTCHA information and the second CAPTCHA information are displayed on a same screen or consecutive screens, and
    wherein first CAPTCHA information for distinguishing between a person and a machine is provided again together with second CAPTCHA information for deciding dyschromatopsia when an authentication of the user fails.

5. The dyschromatopsia compensation apparatus of claim 4, wherein the processor is configured to change color information of contents based on the dyschromatopsia information when the user has the dyschromatopsia.

6. The dyschromatopsia compensation apparatus of claim 4, wherein the processor is configured to change texture information of contents based on the dyschromatopsia information when the user has the dyschromatopsia.

7. A dyschromatopsia deciding method of a program for displaying contents, the method comprising:
    providing first completely automated public turing test to tell computers and humans apart (CAPTCHA) information for distinguishing between a person and a machine together with second CAPTCHA information for deciding dyschromatopsia;
    receiving first CAPTCHA input information corresponding to the first CAPTCHA information and second CAPTCHA input information corresponding to the second CAPTCHA information together with authentication information;
    authenticating a user based on the first CAPTCHA input information and deciding dyschromatopsia of the user based on the second CAPTCHA input information; and storing a decision result of the dyschromatopsia in response to a decision that the user has the dyschromatopsia, wherein the first CAPTCHA information and the second CAPTCHA information are displayed on a same screen or consecutive screens, and wherein first CAPTCHA information for distinguishing between a person and a machine is provided again together with second CAPTCHA information for deciding dyschromatopsia when an authentication of the user fails.

8. The dyschromatopsia deciding method of claim 7, wherein the first CAPTCHA information and the second CAPTCHA information include at least one of a text CAPTCHA, an image CAPTCHA, and a slide CAPTCHA.

9. The dyschromatopsia deciding method of claim 7, wherein the deciding comprises:

authenticating the user based on the first CAPTCHA input information; and deciding dyschromatopsia of the user based on the second CAPTCHA input information when an authentication of the user is successful.

10. A non-transitory computer-readable storage medium storing instructions that, when executed by a processor, cause the processor to perform the dyschromatopsia deciding method of claim 7.

11. A dyschromatopsia compensation method of a program for displaying contents, the method comprising:

providing a screen for requesting authentication information of a user;

authenticating a user based on the authentication information;

loading prestored dyschromatopsia information of the user when an authentication of the user is successful; and changing a content display scheme of a program based on the dyschromatopsia information, wherein the dyschromatopsia information of the user is acquired based on second completely automated public turing test to tell computers and humans apart (CAPTCHA) input information received in correspondence to second CAPTCHA information for deciding dyschromatopsia provided together with first CAPTCHA information for distinguishing between a person and a machine, and the first CAPTCHA information and the second CAPTCHA information are provided together on the screen, wherein the first CAPTCHA information and the second CAPTCHA information are displayed on a same screen or consecutive screens, and wherein first CAPTCHA information for distinguishing between a person and a machine is provided again together with second CAPTCHA information for deciding dyschromatopsia when an authentication of the user fails.

12. The dyschromatopsia compensation method of claim 11, wherein the first CAPTCHA information and the second CAPTCHA information are displayed on a same screen or consecutive screens, and first CAPTCHA information for distinguishing between a person and a machine and second CAPTCHA information for deciding dyschromatopsia are provided again when an authentication of the user fails.

13. The dyschromatopsia compensation method of claim 11, wherein when the user has the dyschromatopsia, the changing of the content display scheme changes color information of contents based on the dyschromatopsia information.

14. The dyschromatopsia compensation method of claim 11, wherein when the user has the dyschromatopsia, the changing of the content display scheme changes texture information of contents based on the dyschromatopsia information.

15. A non-transitory computer-readable storage medium storing instructions that, when executed by a processor, cause the processor to perform the dyschromatopsia compensation method of claim 11.

* * * * *